United States Patent [19]
Reynolds

[11] Patent Number: 5,431,911
[45] Date of Patent: Jul. 11, 1995

[54] SKIN TREATMENT COMPOSITION

[76] Inventor: Diane S. Reynolds, 1231 Westwood La., Fairmont, W. Va. 26554

[21] Appl. No.: 78,848

[22] Filed: Jun. 21, 1993

[51] Int. Cl.$^6$ .............................................. A61K 6/00
[52] U.S. Cl. ................................... 424/401; 424/195.1
[58] Field of Search ...................... 424/401, 195.1, 63, 424/359

[56] References Cited

U.S. PATENT DOCUMENTS

| | | | |
|---|---|---|---|
| 920,824 | 5/1909 | Clark | 514/847 |
| 4,342,743 | 8/1982 | Panton-Moore | 424/61 |
| 4,395,424 | 7/1983 | Veney | 424/359 |
| 4,569,839 | 2/1986 | Grollier et al. | 424/74 |
| 4,694,021 | 9/1987 | Schweiger | 515/580 |
| 5,153,230 | 10/1992 | Jaffery | 514/847 |
| 5,165,915 | 11/1992 | Tokubo et al. | 424/63 |
| 5,266,318 | 11/1993 | Taylor-McCord | 424/195.1 |

Primary Examiner—Thurman K. Page
Assistant Examiner—William E. Benston, Jr.
Attorney, Agent, or Firm—Richard Littman

[57] ABSTRACT

A skin treatment composition in the form of a cosmetic paste for beautifying the skin and maintaining it in a healthy state which comprises almond meal and/or oatmeal, a clay mineral, tincture of benzoin and witch hazel. In an alternate skin treatment composition, a peroxide or lemon juice is substituted for the witch hazel component to provide a composition which is effective for the removal of surface blemishes or for bleaching purposes.

11 Claims, No Drawings

SKIN TREATMENT COMPOSITION

BACKGROUND OF THE INVENTION

1. Field of the Invention

The present invention relates generally to cosmetic compositions for the treatment and care of human skin. More particularly, this invention pertains to a skin treatment composition in the form of a paste for maintaining the skin in a healthy state by providing adequate moisture and essential nutrients thereto.

2. Description of the Prior Art

There are numerous skin care preparations on the market today which have been designed to promote healthy and youthful-looking skin. Many such preparations contain an emollient or provide a moisturizing effect to protect the skin against dryness and wrinkling, which are usually the result of over-exposure to solar radiation, as well as the normal aging process. Other skin preparations have been formulated to exhibit antiseptic, astringent and soothing properties; while still other such formulations are intended to improve skin texture, restore vitamins and proteins, and obscure skin blemishes, for example. However, experience has demonstrated that many of these skin treatment compositions are ineffective for the asserted purposes, relatively unstable, complicated to prepare and require expensive or exotic ingredients.

Exemplary of the cosmetic facial preparations available in the patent literature is U.S. Pat. No. 920,824 to Clark (issued May 4, 1909), which discloses a composition for use as a facial bleacher and whitener comprising cucumber juice, alcohol, powered soap, tincture of benzoin, oil of almonds and boric acid. More recently, U.S. Pat. No. 4,395,424 to Veney (issued Jul. 26, 1983) sets forth a cosmetic cream preparation for cleansing, smoothing and moisturizing the skin containing a mixture of water, non-fat dry milk solids, witch hazel and olive oil as the essential ingredients. In addition, U.S. Pat. No. 4,569,839 to Grollier et al. (issued Feb. 11, 1986) describes cosmetic compositions for the treatment of skin consisting of pulverized particles of at least one plant and a cohesion agent to maintain the homogeneity of the composition.

U.S. Pat. No. 5,153,230 to Jeffery is also exemplary of the prior art which sets forth skin treatment preparations of a rather complex formulation. This patent describes a topical skin cream comprising glycolic acid, vitamins A and E palmitate, in combination with a carrier which includes one or more preservatives, emollients, emulsifying agents, thickening agents and humectants.

SUMMARY OF THE INVENTION

In view of the foregoing considerations, it is an object of the present invention to provide a cosmetic skin treatment composition which is markedly effective in beautifying the skin and maintaining it in a healthy state.

It is a further object of the invention to provide a skin treatment formulation which soothes and moisturizes the skin to improve its texture and protect it against dryness and wrinkles.

It is a still further object of the invention to provide a cosmetic facial preparation which removes skin blemishes and restores vital nutrients to the skin.

It is among the further objects of the present invention to provide a cosmetic composition for the treatment of skin which may be readily formulated without requiring costly ingredients or complicated preparation procedures.

These and other objects are accomplished in accordance with a particular embodiment of the present invention which provides skin treatment compositions in the form of a cosmetic paste comprising a mixture consisting essentially of a grain product selected from the group consisting of almond meal, oatmeal and mixtures thereof, a clay mineral, tincture of benzoin and witch hazel. The essential components of the present composition readily intermix to form a homogeneous mixture having a paste consistency suitable for topical application to the skin. The present components are combined in such relative proportionalities so as to bring about a marked beautifying effect to the skin by providing adequate moisture and essential nutrients thereto.

In an alternative embodiment of the present invention, a peroxide or lemon juice may be substituted for the witch hazel component to provide a composition which is effective for the removal of surface blemishes or for bleaching purposes.

The foregoing and other aspects, advantages and objects of the invention may be more fully appreciated by reference to the following detailed description.

DETAILED DESCRIPTION OF THE PREFERRED EMBODIMENTS

In accordance with one embodiment of the present invention, the skin treatment composition comprises a substantially homogeneous paste consisting essentially of the following ingredients in the following relative proportions:

about 25-35% by volume of almond meal and/or oatmeal,
about 10-20% by volume of a cosmetic clay,
about 0.5-2% by volume of tincture of benzoin, and
about 35-55% by volume of witch hazel.

The meal ingredient of the present composition is produced by grinding or pulverizing the respective grain seeds to a finely divided state. These milled grain products may be obtained commercially as powders and because of their naturally inherent nutrient content provide numerous beneficial properties to the skin. Due to its ready availability and dispersibility, colloidal oatmeal is preferred in this regard.

The argillaceous or clay constituent, which serves as both an absorbent and a base for the composition, should be essentially non-toxic and dermatologically safe. Representative of such substances include China clay, colloidal kaolin, bentonite and other aluminum silicates, Fuller's earth, a nonplastic magnesium-containing kaolin, is particularly preferred for this purpose.

The tincture of benzoin component, a balsamic gum solution, is included for its highly effective skin-protective and antiseptic properties. However, since this chemical component can cause allergic skin reactions in some cases, its use is limited to relatively small amounts. Preferably, about 1% of the tincture of benzoin based on the total unit volume of the composition, or about 5 drops of this benzoin solution per teaspoon of the cosmetic clay constituent, is present in the compositions.

The remaining liquid component of the present composition is witch hazel, which is included for its astringent properties. It will be appreciated that both liquid components of the composition are relatively inexpensive and readily available commercially.

In accordance with a specific aspect of the present embodiment, the cosmetic composition consists essentially of about 30% by volume of almond meal and/or oatmeal, about 15% by volume of a cosmetic clay, about 1% by volume of tincture of benzoin, and about 45% by volume of witch hazel.

According to another embodiment of the present invention, a skin treatment composition is differently formulated to additionally provide bleaching properties. In this particular embodiment, the composition comprises a substantially homogeneous paste consisting essentially of the following ingredients in the designated relative proportions:

about 25-35% by volume of almond meal and/or oatmeal,
about 10-20% by volume of a cosmetic clay,
about 0.5-2% by volume of tincture of benzoin, and
about 35-55% by volume of a skin bleaching agent.

Suitable bleaching agent components include diluted hydrogen and sodium peroxide solutions, and lemon juice. Representative of a specific aspect of this particular embodiment, the cosmetic composition consists essentially of about 30% by volume of almond meal and/or oatmeal, about 15% by volume of a cosmetic clay, about 1% by volume of tincture of benzoin, and about 45% by volume of a skin bleaching agent.

The preparation of the skin treatment compositions may be achieved very economically and rapidly. In preparing both embodiments of the present invention, the liquid and dry components of the cosmetic compositions are generally prepared separately and then mixed together. Preferably, the meal and clay components are intimately mixed together first at a meal/clay volume ratio of about 2:1 to form a dry powder. This dry mixture and the liquid portion of cosmetic composition are then mixed together in substantially equal amounts until the powder portion is completely dissolved to form a lump free paste. The resultant paste possesses a consistency which permits it to be caked onto the skin area where treatment is desired. Thus, the present compositions preferably have the texture of a face pack or mask. These facial formulations can be prepared according to the present procedure just before use or may then be placed in any suitable container, preferably a sealable jar or tube, until ready for use. The present cosmetic compositions maintain their effectiveness for extended periods of time and do not solidify upon storage in a suitable container nor do the dry constituents settle out.

The paste compositions of the present invention are particularly adapted for topical application in effective amounts directly to the facial and neck area. In a typical application procedure, the treatment area of the skin is thoroughly cleansed and then gently patted dry with a soft towel. If a cleansing solution is used, it should be completely removed prior to drying the skin. The paste is then sparsely or liberally applied to the throat and face by hand or with a cosmetic brush. Care should be exercised during application of the facial composition to avoid contact with areas close to the eyes. The paste composition is allowed to dry and hardened to form a mask, which usually remains on the facial and neck areas for approximately 20 minutes. The hardened cosmetic composition can then be removed by first rinsing with warm water, followed by a cold water rinse. This procedure nay be repeated nightly, usually for 5 or 6 nights to promote and maintain the skin in a healthy state.

It has been found that the essential components of the present skin treatment compositions combine to produce a certain synergistic effect, whereby an overall skin beautifying result is obtained. The compositions are also effective in restoring moisture and essential nutrients to the skin, and leaves it firmer in texture and appearance. In addition, the skin may show a noticeable color difference in that it becomes lighter after repeated applications, Alternatively, when a bleaching agent is incorporated in accordance with the particular embodiment discussed hereinabove, the compositions may be used as an effective facial bleacher and whitener to remove tan, freckles and other superficial blemishes from the skin.

It should be understood that there may be various changes and modifications of the representative embodiments herein chosen for purposes of description without departing from the spirit and scope of the invention. Accordingly, the foregoing description is not to be interpreted as restrictive of the invention beyond that necessitated by the following claims.

I claim:

1. A cosmetic skin treatment composition consisting essentially of:
   about 25-35% by volume of a grain product selected from the group consisting of almond meal, oatmeal and mixtures thereof,
   about 10-20% by volume of a cosmetic clay,
   about 0.5-2% by volume of tincture of benzoin, and
   about 35-55% by volume of witch hazel.

2. The composition of claim 1 wherein the grain product is colloidal oatmeal.

3. The composition of claim 1 wherein said cosmetic clay is fuller's earth.

4. The composition of claim 1 wherein the paste consists essentially of about 30% by volume of the almond meal and/or the oatmeal, about 15% by volume of the cosmetic clay, about 1% by volume of tincture of benzoin, and about 45% by volume of witch hazel.

5. A cosmetic skin treatment composition consisting essentially of: about 25-35% by volume of a grain product selected from the group consisting of almond meal, oatmeal and mixtures thereof,
   about 10-20% by volume of a cosmetic clay,
   about 0.5-2% by volume of tincture of benzoin, and
   about 35-55% by volume of a skin bleaching agent.

6. The composition of claim 5 wherein the grain product is colloidal oatmeal.

7. The composition of claim 5 wherein said cosmetic clay is fuller's earth.

8. The composition of claim 5 wherein the skin bleaching agent is selected from the Group consisting of a dilute hydrogen peroxide solution, a sodium peroxide solutions and lemon juice.

9. The composition of claim 5 wherein the paste consists essentially of about 30% by volume of the almond meal and/or the oatmeal, about 15% by volume of the cosmetic clay, about 1% by volume of tincture of benzoin, and about 45% by volume of the skin bleaching agent.

10. A method of treating human skin which comprises the steps of topically applying an effective amount of the composition of claim 1 to said skin, allowing the composition to harden, and removing the composition.

11. A method of treating human skin which comprises the steps of topically applying an effective amount of the composition of claim 5 to said skin, allowing the composition to harden, and removing the composition.

* * * * *